United States Patent [19]

Zhang et al.

[11] Patent Number: 5,942,605
[45] Date of Patent: Aug. 24, 1999

[54] 5-IMINO-13-DEOXY ANTHRACYCLINE DERIVATIVES, THEIR USES, AND PROCESSES FOR PREPARING THEM

[75] Inventors: Xini Zhang, Hoover, Ala.; Richard D. Olson, Nampa, Id.

[73] Assignee: GEM Pharmaceuticals, Inc., Pelham, Ala.

[21] Appl. No.: 09/033,659

[22] Filed: Mar. 3, 1998

[51] Int. Cl.$^6$ .................................................. C07H 15/24
[52] U.S. Cl. ............................................ 536/6.4; 514/34
[58] Field of Search ................................. 514/34; 536/6.4

[56] References Cited

U.S. PATENT DOCUMENTS

| | | |
|---|---|---|
| 4,067,969 | 1/1978 | Penco et al. . |
| 4,088,569 | 5/1978 | Douglas . |
| 4,134,903 | 1/1979 | Masi et al. . |
| 4,247,545 | 1/1981 | Cassinelli et al. . |
| 4,309,503 | 1/1982 | Cassinelli et al. . |
| 4,345,070 | 8/1982 | Suarato et al. . |
| 4,353,894 | 10/1982 | Acton et al. . |
| 4,411,834 | 10/1983 | Cassinelli et al. . |
| 4,465,671 | 8/1984 | Angelucci et al. . |
| 4,515,720 | 5/1985 | Hauser et al. . |
| 4,839,346 | 6/1989 | Bargiotti et al. . |
| 4,891,360 | 1/1990 | Angelucci et al. . |
| 4,939,282 | 7/1990 | Angelucci et al. . |
| 4,985,548 | 1/1991 | Caruso et al. . |
| 4,987,126 | 1/1991 | Bargiotti et al. . |
| 5,037,970 | 8/1991 | Angelucci et al. . |
| 5,138,042 | 8/1992 | Angelucci et al. . |
| 5,412,081 | 5/1995 | Angelucci et al. . |
| 5,532,218 | 7/1996 | Bargiotti et al. . |

FOREIGN PATENT DOCUMENTS

| | | |
|---|---|---|
| 2238540 | 6/1991 | United Kingdom . |

OTHER PUBLICATIONS

Edward M. Acton, "Unresolved Structure—Activity Relationships in Anthracycline Analogue Development," *Anthracycline Antibiotics*, Chapter 1, pp. 1–5.

Smith, T.H., et al., "Adriamycin Analogues. 2. Synthesis of 13–Deoxyanthracyclines," *Journal of Medicinal Chemistry*, vol. 21, No. 3, 1978, pp. 280–283.

*Primary Examiner*—James O. Wilson
*Assistant Examiner*—Howard Owens
*Attorney, Agent, or Firm*—Pollock, Vande Sande & Amernick

[57] ABSTRACT

5-imino-13-deoxy anthracycline derivatives, medical uses of 5-imino-13-deoxy anthracycline derivatives and methods for preparing 5-imino-13-deoxy anthracycline derivatives.

20 Claims, No Drawings

5-IMINO-13-DEOXY ANTHRACYCLINE DERIVATIVES, THEIR USES, AND PROCESSES FOR PREPARING THEM

FIELD OF THE INVENTION

The invention relates to 5-imino-13-deoxy anthracycline derivatives, the medical uses of 5-imino-13-deoxy anthracycline and methods for preparing 5-imino-13-deoxy anthracycline derivatives.

BACKGROUND OF THE INVENTION

The most well-known anthracycline anticancer drugs are doxorubicin and daunorubicin, which contain a 13-keto group and a 5-keto group. Doxorubicin, disclosed in U.S. Pat. No. 3,590,028, has a wide spectrum of anticancer utility and is used in the treatment of leukemias, lymphomas, and solid tumors. Daunorubicin, disclosed in U.S. Pat. No. 3,616,242, is useful in the treatment of acute leukemias. However, the utility of these drugs is limited by a serious side effect of cardiotoxicity so that the total amount of drug that can be given to a patient cannot exceed 550 mg/M$^2$ (E. A. Lefrak et al., Cancer, 32:302, 1973). Even at or near the recommended maximum total cumulative dosage (430–650 mg/M$^2$) significant and persistent heart dysfunction occurs in 60% of patients and 14% develop congestive heart failure (A. Dresdale et al., Cancer, 52:51, 1983). Thus, while these drugs are useful to inhibit the growth of cancerous tumors, the patient may die of congestive heart failure because of the severe cardiotoxic side effect of the drugs.

Some researchers believe that the cardiotoxicity is a result of free radical generation by the quinone moiety of the anthracycline molecule (J. Dorowshow et al., J. Clin. Invest., 68:1053, 1981; D. V. Unverferth et al., Cancer Treat. Rev., 9:149, 1982; J. Goodman et al., Biochem. Biophys. Res. Commun., 77:797, 1977; J. L. Zweier, J. Biol. Chem., 259:6056, 1984). On the other hand, there is good evidence that free radical generation may not be the only mechanism of cardiotoxicity because the drugs still produce cardiac damage in the presence of free radical scavengers (J. F. VanVleet et al., Am. J. Pathol., 99:13, 1980; D. V. Unverferth et al., Am. J. Cardiol., 56:157, 1985; C. Myers et al., Seminars in Oncology, 10:53, 1983; R. H. M. Julicher et al., J. Pharm. Pharmacol., 38:277, 1986; E.A. Porta et al., Res. Comm. Chem. Pathol Pharmacol., 41: 125, 1983).

It has also been found that inhibition of free radical generation does not eliminate the cardiotoxicity of these anthracyclines (P. S. Mushlin et al., Fed. Proc., 45:809, 1986). This research shows, instead, that the cardiotoxicity of doxorubicin and daunorubicin, as manifested by a reduction in myocardial contractility, is also dependent upon the metabolic reduction of the 13-keto moiety to a 13-dihydro metabolite. In test systems where doxorubicin is not metabolized appreciably to the 13-dihydro compound cardiotoxic effects are observed only at very high concentrations (200–400 micrograms/ml) (P. S. Mushlin et al., Fed. Proc., 44:1274, 1985; R. D. Olson et al., Fed. Proc., 45:809, 1986). In contrast, the 13-dihydro metabolites, doxorubicinol and daunorubicinol, produce cardiotoxicity in these same test systems at relatively low concentrations (1–2 micrograms/ml, R. D. Olson et al., Proceed. Am. Assoc. Cancer Res., 26:227, 1985; R. D. Olson et al., Proceed. Am. Assoc. Cancer Res., 28:441, 1987).

If doxorubicin is allowed to remain in the test systems even for short periods of time some metabolic conversion occurs and the 13-dihydro metabolite is formed in sufficient quantity so that cardiotoxicity begins to develop (L. Rossini et al., Arch. Toxicol. suppl., 9:474, 1986; M. Del Tocca et al., Pharmacol. Res. Commun., 17:1073, 1985). Substantial evidence has, thus, accumulated that the cardiotoxicity of drugs such as doxorubicin and daunorubicin results from the potent cardiotoxic effects produced by their 13-dihydro metabolites (P. Mushlin et al., Rational Drug Therapy, 22:1, 1988; S. Kuyper et al., FASEP Journal, 2:A1133, 1988; R. Boucek et al., J. Biol. Chem., 262:15851, 1987; and R. Olson et al., Proc. Natl. Acad. Sci., 85:3585, 1988).

The present invention makes use of the fact that the 13-deoxy forms of doxorubicin, daunorubicin, or other similar anthracyclines will not be metabolically converted to cardiotoxic 13-dihydro forms, and that the 5-keto group is modified to a form that will be less likely to generate free radicals, thus providing a means for administering compounds of the present invention in noncardiotoxic amounts without limitation of total cumulative dosage.

SUMMARY OF THE INVENTION

The present invention aims to provide new 5-imino-13-deoxy anthracycline derivatives that have fewer side effects.

Accordingly, an object of the present invention is to provide processes for preparing 5-imino-13-deoxy anthracycline derivatives.

In accordance with these and other objects and advantages, the preferred aspects of the present invention provide a process for the preparation of 5-imino-13-deoxy anthracycline derivatives.

Generally, anthracyclines of the formula I

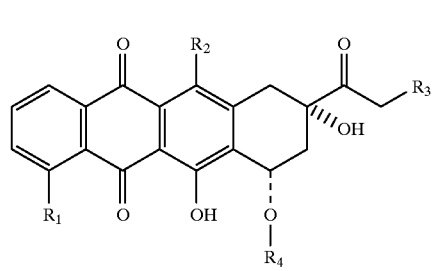

wherein $R_1$, $R_2$, and $R_3$ are H or OH and $R_4$ is a sugar moiety, are readily converted to 13-tosylhydrazones according to known methods. Anthracycline 13-tosylhydrazones are reduced to 13-deoxy anthracycline derivatives with sodium cyanoborohydride under acidic conditions. The products are then purified by preparative chromatography without extraction steps. The purified 13-deoxy anthracycline derivatives are converted to N-Boc derivatives and then treated with $NH_3$ to produce N-Boc-5-imino-13-deoxy anthracyclines. Removal of N-Boc under acidic conditions produces 5-imino-13-deoxy anthracycline derivatives. The processes have been found to have a yield of from about 50% to about 60%.

Additional preferred aspects of the present invention provide a process for the preparation of 5-imino-13-deoxy deoxyanthracycline derivatives. The process includes forming an acidic solution of anthracycline 13-tosylhydrazone with cyanoborohydride. The solution is gently refluxed. The reaction mixture is cooled. A small amount of water is added to the solution, followed by a halocarbon solvent. The mixture is filtered. The filtrate is subjected to preparative chromatography to isolate the 13-deoxy anthracycline derivatives. The purified derivatives are protected by a tert-butoxycarbonyl group to form 3'-N-Boc derivatives, which are then treated with ammonia to form 3'-N-Boc-5-imino-13-deoxyanthracyclines. Removing the amino-protecting group under acidic conditions produces 5-imino-13-deoxyanthracyclines, which are then purified by chromatography.

Further preferred aspect of the present invention provide a process for the preparation of 5-imino-13-deoxy anthracycline derivatives. The process includes forming a solution by dissolving about 1 g of doxorubicin 13-tosylhydrazone hydrochloride and about 2.4 g of p-toluene sulfonic acid in about 50 mL of anhydrous methanol. About 0.8 g of sodium cyanoborohydride is added to the solution.

The solution is heated to a temperature of from about 68° C. to about 72° C. The solution is gently refluxed for about one hour under a nitrogen atmosphere.

The reaction mixture is concentrated to about 20 ml. The reaction mixture is cooled in a freezer to a temperature of from about 0° C. to about 40° C.

About 0.5 ml of water is added to the reaction mixture. About 200 ml of chloroform is added to the reaction mixture. Anhydrous sodium sulfate is added to the reaction mixture. Salts are filtered out.

The filtrate is run through a silica gel column. The column is further washed with chloroform/methanol until the eluate is colorless.

A fraction containing the product is eluted with methanol. The methanol eluate is evaporated. Residue resulting from the evaporation is dissolved in 30% acetonitrile in ammonium formate buffer.

The product is isolated by preparative HPLC using a phenyl column. The product is separated from other impurities using an acetonitrile/ammonium formate gradient. The HPLC purified fraction is then diluted with about the same volume of water as the fraction collected and this solution is run through a preparative phenyl HPLC column. The column is eluted with water to remove the salt. The product is eluted with methanol. The methanol eluate is concentrated and the same product is precipitated by the addition of ethyl ether. The solid product is recovered by filtration to yield about 600 mg of 13-deoxy doxorubicin.

About 600 mg of purified 13-deoxy doxorubicin is dissolved in about 60 ml of methylene chloride and about 10 ml of water and treated with about 180 mg of potassium hydrogen carbonate and about 180 mg of di-tert-butyldicarbonate at room temperature for about 2 hours. The organic solution is separated, washed with water and dried with anhydrous sodium sulfate. The solution is evaporated to dryness. The residue is dissolved in about 100 ml of anhydrous methanol. The solution is kept saturated with ammonia at about 0° C. to about 4° C. for about 48 hours. The solvent and ammonia are removed under vacuum to give 3'-N-Boc-5-imino-13-deoxydoxorubicin. The 3'-N-Boc-5-imino-13-deoxy doxorubicin obtained above is treated with about 60 ml of anhydrous methanol containing about 0.1 M hydrogen chloride at room temperature for about 2 hours to remove the 3'-N-Boc group. The resulting solution is concentrated to about 5 ml.

The concentrated solution is isolated by preparative HPLC with a phenyl column. The product is separated from other impurities using an acetonitrile/ammonium formate gradient. The HPLC-purified fraction is diluted with approximately an equal volume of water, injected onto a preparative HPLC phenyl column and rinsed with water to remove the salts. The product is then eluted with methanol. The methanol eluate is acidified with about 0.5 ml of hydrogen chloride in ethyl ether. The solution is then concentrated to about 5 ml. About 10 ml of ethyl ether is added to precipitate the product. The precipitate is filtered to yield about 360 mg of 5-imino-13-deoxy doxorubicin hydrochloride.

The present invention also provides compounds having the following formula:

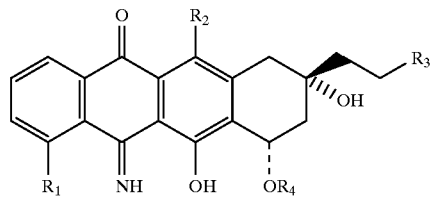

wherein $R_1$, $R_2$, and $R_3$ are H, OH, or OMe and $R_4$ is a sugar moiety.

Furthermore, the present invention provides a pharmaceutical composition including at least one 5-imino-13-deoxy anthracycline derivative.

Still further, the present invention provides a method of treating cancer, including leukemias, lymphomas, and solid tumors, the process including the step of administering an effective amount of at least one 5-imino-13-deoxy anthracycline derivative.

Still other objects and advantages of the present invention will become readily apparent to those skilled in the art from the following description. The detailed description shows and describes only preferred embodiments of the invention so as to illustrate the best mode contemplated for carrying out the invention. As those skilled in the art will realize, the invention includes other and different embodiments. Details of the invention may be modified in various respects, without departing from the invention. Accordingly, the drawings and description should be regarded as illustrative in nature and not as restrictive.

DETAILED DESCRIPTION OF THE INVENTION

The present invention provides 5-imino-13-deoxy anthracycline derivatives, their uses, and methods for forming 5-imino-13-deoxy anthracycline derivatives. FIG. 3 provides examples of 5-imino-13-deoxy anthracycline derivatives that may be synthesized according to the present invention. As discussed above, compounds such as those shown in FIG. 3 are known to have anti-tumor properties. The compounds also have fewer side effects.

The processes of the present invention may be carried out at a temperature of from about 0° C. to about 75° C. Preferably, the processes are carried out at a temperature of from about 65° C. to about 75° C. More preferably, the process are carried out at a temperature of from about 68° C. to about 72° C. Temperatures over about 72° C. typically result in decomposition of the reactants and products.

The process of the present invention includes a number of general conditions. For example, the reduction reaction preferably is carried out in acidic conditions. In other words, the pH should be about 7.0 or less. Known processes for preparing the above compounds, which employ basic conditions within the reaction mixture, have been found to cause decomposition of the reactants and products.

Additionally, both oxygen and water should be excluded from the reduction reaction. Preferably, the reaction is conducted in a nitrogen or inert gas atmosphere, using anhydrous solvents.

Additionally, the amination reaction should be carried out at about 0–4° C. Higher temperatures may cause decomposition of the reactants and products.

Additionally, water should be excluded from the amination reaction. Preferably, the reaction is conducted in anhydrous solvents.

Additionally, water should be excluded from the hydrolysis reaction. Preferably, the reaction is conducted in anhydrous solvents.

In accordance with the above, the present invention provides processes for preparing compounds of the general formula I above.

The following provides an example of the transformation of the molecule as it progresses through the process.

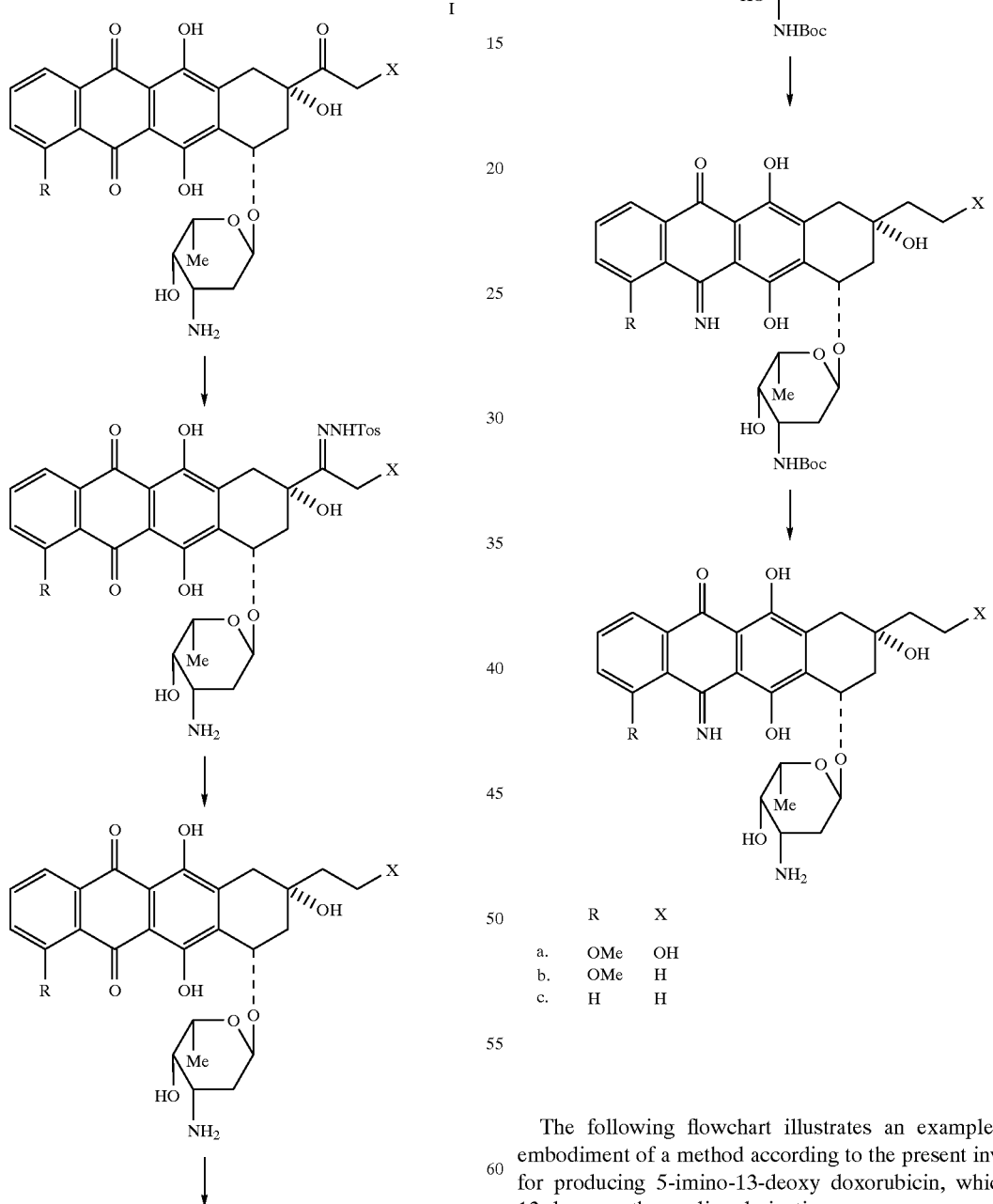

| | R | X |
|---|---|---|
| a. | OMe | OH |
| b. | OMe | H |
| c. | H | H |

The following flowchart illustrates an example of an embodiment of a method according to the present invention for producing 5-imino-13-deoxy doxorubicin, which is a 13-deoxy anthracycline derivative.

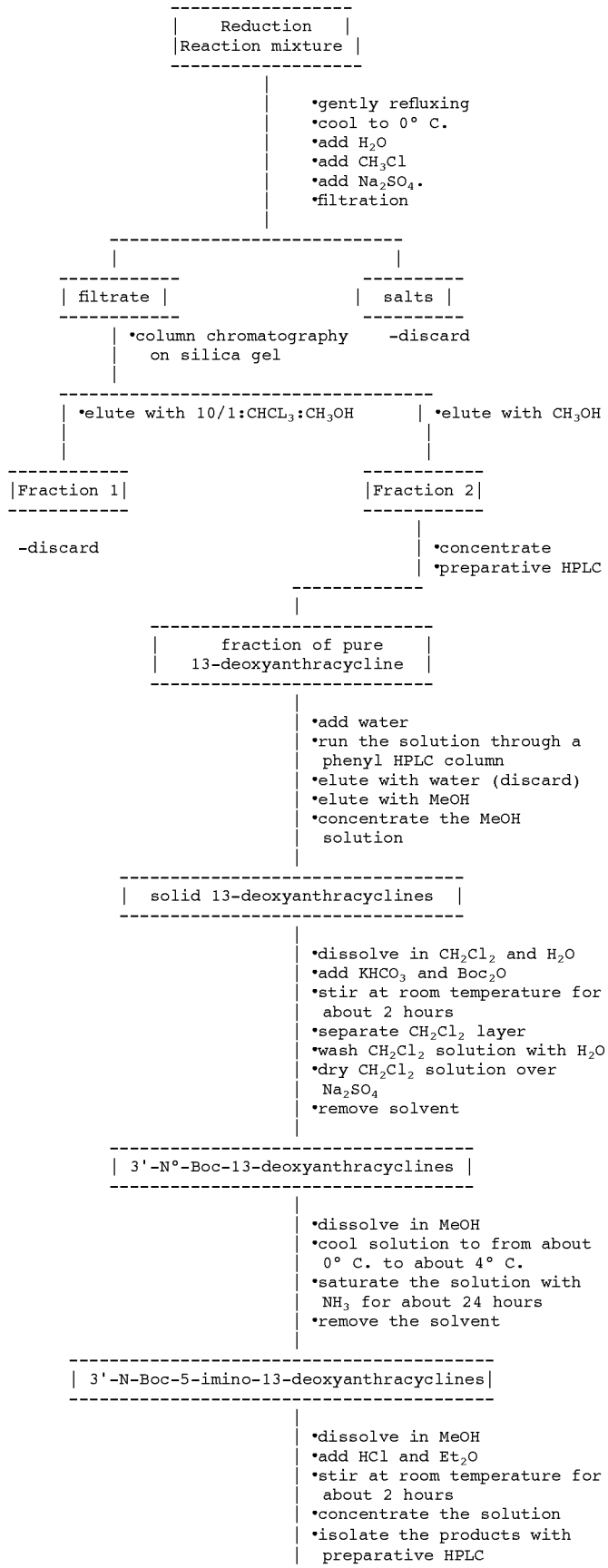

```
-----------------------------------------------
|fraction of 5-imino-13-deoxyanthracyclines|
-----------------------------------------------
                |
                | •add water
                | •run the solution through a
                |   phenyl HPLC column
                | •elute with water (discard)
                | •elute with MeOH
                | •add HCl/Et2O
                | •concentrate MeOH solution
                | •add Et2O
                | •filter the precipitate
-----------------------------------------------
| solid 5-imino-13-deoxyanthracyclines hydrochloride |
-----------------------------------------------
```

The following represents examples of anthracycline derivatives, the synthesis of which is disclosed herein.

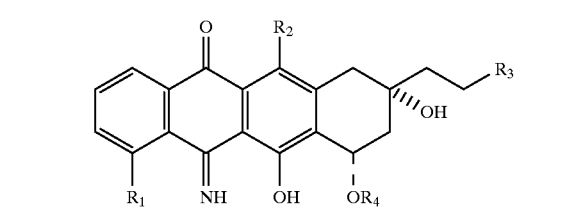

| $R_1$ | $R_2$ | $R_3$ | $R_4$ | Analog of |
|---|---|---|---|---|
| OMe | OH | OH | 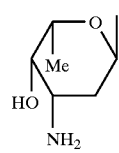 | doxorubicin |
| OMe | OH | H | 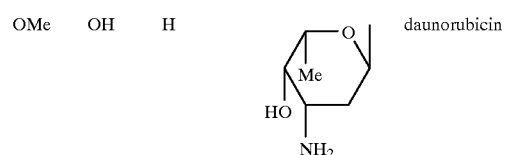 | daunorubicin |
| OH | OH | H | 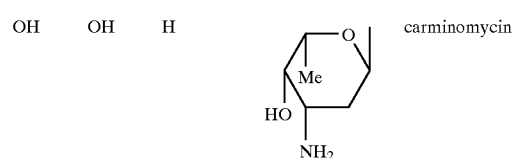 | carminomycin |
| OMe | OH | OH | 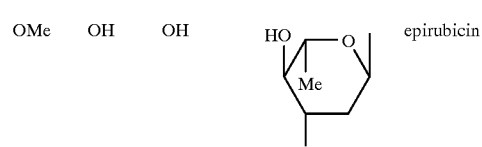 | epirubicin |
| H | OH | H | 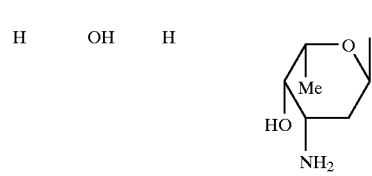 | idarubicin |

-continued

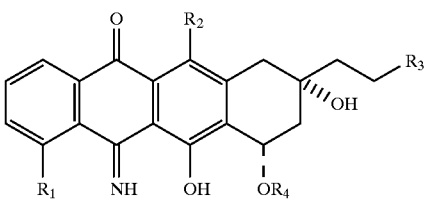

| $R_1$ | $R_2$ | $R_3$ | $R_4$ | Analog of |
|---|---|---|---|---|
| H | OH | OH | 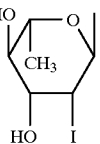 | annamycin |

In the compounds, $R_4$ may be a modified version of different anthracycline analogues. Also, The D ring may be fluorinated.

Generally, processes according to the present invention include forming an acidic solution of a 5-imino-13-deoxy anthracycline. The solution is gently refluxed. Then, the reaction mixture may be cooled. According to one example, the reaction mixture is cooled to a temperature of from about 0° C. to about 4° C. A small amount of water may then be added to hydrolyze the product. A halocarbon solvent may be added to the reaction mixture. The halocarbon solvent may be cold. For example, the halocarbon solvent may be at a temperature of from about 0° C. to about 4° C. An example of a halocarbon solvent that may be utilized is chloroform. The reaction mixture may then be filtered after addition of anhydrous sodium sulfate. The filtration may also take place at a reduced temperature. For example, the filtration may take place at a temperature of from about 4° C. to about 15° C.

Addition of the water described above preferably initiates a hydrolysis. Any excess water may be removed by the addition of anhydrous sodium sulfate. The inorganic salts preferably are then filtered out of the reaction mixture. The filtrate may be subjected to column chromatography on silica gel. Hydrophobic impurities may be isolated by eluting with less polar solvents. 13-deoxy anthracycline products may then be eluted and the elute further purified.

The purified 13-deoxy anthracycline derivatives may be dissolved in a mixed solution of methylene chloride and water containing a base and di-tert-butyl dicarbonate. The solution may be stirred at about room temperature for about 2 hours. The organic solution may be isolated and washed with water. Then, the solvent may be removed and the residue may be dissolved in an alcohol solvent. The alcohol solution may be saturated with ammonia at about 0° C. to about 4° C. for about 24 hours. The solvent may be removed and the dry residue may be treated with an acidic alcoholic solvent at about room temperature for about 2 hours. The resulting solution may be concentrated and subjected to further purification, then, acidified and precipitated in ether to yield the hydrochloride salts of 5-imino-13-deoxy anthracycline.

Preferably, the processes according to the present invention include forming a solution of anthracycline 13-tosylhydrazones in anhydrous methanol with p-toluenesulfonic acid and sodium cyanoborohydride. The solution is refluxed gently under nitrogen and then cooled. Water is added, followed by chloroform. Salts precipitated are filtered and the filtrate is isolated on a silica gel column. The hydrophobic impurities resulted from decomposition are eluted with chloroform and methanol mixed solution. The products, 13-deoxy anthracyclines, are eluted with methanol. The methanol elute is further purified by preparative HPLC.

The purified 13-deoxy anthracyclines are dissolved in a mixture of methylene chloride and water and treated with potassium hydrogen carbonate and di-tert-butyl dicarbonate. The solution is stirred at about room temperature for about 2 hours. The organic layer is isolated, washed with water and dried over anhydrous sodium sulfate. The solvent is then removed under vacuum. The residue is dissolved in anhydrous methanol and kept saturated with ammonia at about 0° C. to about 4° C. for about 48 hours. The methanol and ammonia are removed from the reaction product, which is treated with a dilute acid in alcohol at about room temperature for about 2 hours to give the compound 5-imino-13-deoxy anthracycline. That compound, in solution, is concentrated and then purified by preparative HPLC to remove impurities and then salts. The product is eluted with methanol, acidified and precipitated to yield the hydrochloride salt of the 5-imino-13-deoxy anthracycline.

The following provides an example of a process according to the present invention.

EXAMPLE

Preparation of 5-imino-13-deoxy Doxorubicin Hydrochloride

About 1 g of doxorubicin 13-tosylhydrazone hydrochloride and about 2.4 g of p-toluene sulfonic acid are dissolved in about 50 mL of anhydrous methanol. To this solution about 0.8 g of sodium cyanoborohydride is added. The resulting solution is heated to about 68–72° C. and kept at gentle reflux for one hour under nitrogen atmosphere.

Then, the reaction mixture is concentrated to about 20 ml and cooled in a freezer to about 0–4° C. About 0.5 ml of water is added followed by about 200 ml of chloroform. Anhydrous sodium sulfate is added and the salts are filtered after shaking.

The solution is then run through a silica gel column (2.5×5 cm). The column is further washed with chloroform/methanol (10/1) until the eluate is colorless. The bound fraction containing the product is eluted with methanol. The methanol elute is evaporated and residue is dissolved in 30% acetonitrile in ammonium formate buffer (pH=4.0, 0.5%) and isolated by preparative HPLC. A phenyl column is used and separation of the product from the other impurities is achieved by using an acetonitrile/ammonium formate gradient (from 27% to 30% acetonitrile for about 30 min).

The HPLC purified fraction is diluted with about an equal volume of water. The solution is run through a preparative HPLC phenyl column. The column is eluted with water to remove salts. The product is then eluted with methanol. The methanol is concentrated and the product is precipitated by the addition of ethyl ether-containing hydrogen chloride and collected by filtration to give 600 mg of 13-deoxy doxorubicin hydrochloride. The yield is 80%.

TLC: $R_f$=0.38 CH$_3$Cl:MeOH:H$_2$O 30 10 1

U.V. : $\lambda_{max}$=233, 252, 293, 485 nm

MS:

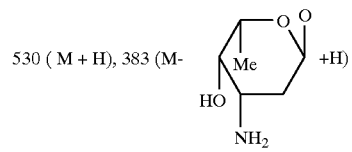

530 (M + H), 383 (M− +H)

$^1$HNMR (methanol d$_4$): (see below) δ1.30 (d, 3H, 6'-CH$_3$), 1.85 (m, 2H, 13-H$_2$), 2.05 (m, 2H, 10-H$_2$), 2.60 (d, 1H, 12-H), 3.05 (d, 1H, 12-H), 3.55 (m, 1H, 5'-H), 3.90 (m, 2H, 14-H$_2$), 4.05 (s, 3H, O—CH$_3$), 4.25 (m, 1H, 4'-H), 4.95 (m, 1H, 3'-H), 5.40 (m, 1H, 1'-H), 7.55 (d, 1H, 3-H), 7.85 (d, 1H, 2-H), and 7.95 (d, H, 1-H).

About 600 mg of purified 13-deoxy doxorubicin is dissolved in about 60 ml of methylene chloride and about 10 ml of water and treated with about 180 mg of potassium hydrogen carbonate and about 180 mg of di-tert-butyldicarbonate at about room temperature for about 2 hours. The organic solution is separated, washed with water and dried over anhydrous sodium sulfate. The solution is evaporated to dryness and the residue is dissolved in about 100 ml of anhydrous methanol. The solution is kept saturated with ammonia at about 0° C. to about 4° C. for about 48 hours. The solvent and ammonia are removed under vacuum to afford 3'-N-Boc-5-imino-13-deoxy doxorubicin, which is treated with about 60 ml of anhydrous methanol-containing 0.1 M hydrogen chloride at about room temperature for about 2 hours to remove the 3'-N-Boc group. The resulting solution is concentrated and the product is isolated by preparative HPLC. The HPLC-purified fraction is diluted with an equal volume of water. The solution is added to a preparative phenyl HPLC column and eluted with water to remove the salts. The product is eluded with methanol. The methanol eluate is acidified with hydrogen chloride in ethyl ether and the solution is concentrated. Ethyl ether is added and the resulting precipitate is filtered to give about 360 mg of 5-imino-13-deoxy doxorubicin hydrochloride.

TLC: $R_f$=0.35

UV: $\lambda_{max}$=222, 251, 310, 544, 585 nm $^1$HNMR (MeOH-da) δ1.30 (d, 3H, 6'-CH$_3$) 1.85 (m, 2H, 13-H$_2$) 2.10 (m, 2H, 10-H$_2$) 2.60 (d, 1H, 12-H) 2.75 (d, 1H, 12-H) 2.95 (d, 1H, 12-H) 3.50 (m, H, 5'-H) 3.90 (m, 2H, 14-H$_2$) 4.15 (s, 3H, O—CH$_3$) 4.25 (m, 1H, 4'-H) 5.10 (m, 1H, 3'H) 5.60 (m, 1H, 1'-H) 7.50 (d, 1H, 3-H) 7.80 (d, 1H, 2-H) 8.05 (d, 1H, 1-H)

MS:

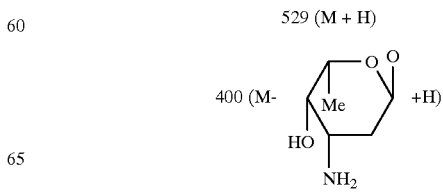

529 (M + H)

400 (M− +H)

-continued

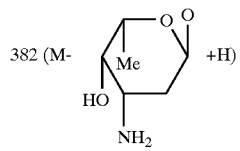

The present invention also provides compounds having the following formula:

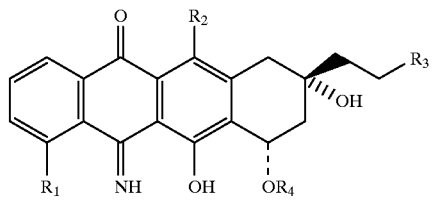

Furthermore, the present invention provides a pharmaceutical composition including at least one 5-imino-13-deoxy anthracycline derivative.

Still further, the present invention provides a method of treating cancer, including leukemias, lymphomas, and solid tumors. The method includes the step of administering an effective amount of at least one 5-imino-13-deoxy anthracycline derivative. The dosages would be similar to known compounds. Due to their similarities to known compounds, those skilled in the art would be able to determine treatment regimens resulting in similar efficacy without undue experimentation. However, as discussed above, the present invention provides for significantly reduced side effects including reduced cardiotoxicity.

The present invention also provides a method of treating AIDS. The method includes the step of administering an effective amount of at least one 5-imino-13-deoxy anthracycline derivative.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

We claim:
1. Compounds having the following formula:

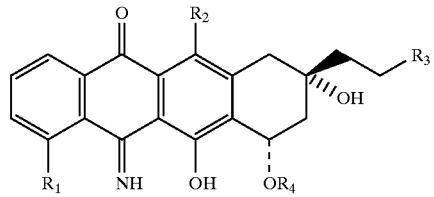

wherein $R_1$, $R_2$ and $R_3$ are each selected from the group consisting of H, OH, and $OCH_3$, and $R_4$ is a sugar moiety selected from the group consisting of

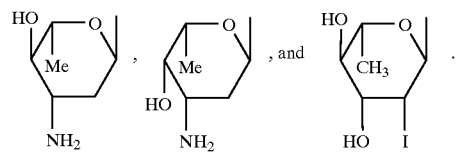

2. A pharmaceutical composition, comprising:
   at least one 5-imino-13-deoxy anthracycline derivative of the formula of claim 1.
3. A process for the preparation of 5-imino-13-deoxy anthracycline derivatives, said process comprising the steps of:
   forming a reduction solution of anthracycline 13-tosylhydrazone in anhydrous methanol with p-toluenesulfonic acid and sodium cyanoborohydride;
   gently refluxing the solution under nitrogen;
   cooling the solution;
   adding water and chloroform to the solution;
   adding anhydrous sodium sulfate;
   filtering the precipitate;
   isolating filtrate on a silica gel column;
   eluting the hydrophobic impurities resulting from decomposition with a mixed solution of chloroform and methanol;
   eluting the 13-deoxy anthracycline products with methanol;
   further purifying the methanol eluate by preparative HPLC;
   forming a solution of the purified 13-deoxyanthracyclines in methylene chloride and water;
   adding potassium hydrogen carbonate and di-tert-butyl carbonate;
   isolating N-Boc-protected products;
   dissolving 3'-N-Boc-13-deoxy anthracyclines in anhydrous methanol;
   cooling the solution;
   saturating the solution with ammonia to carry out an amination of the 3'-N-Boc-13-deoxyanthracyclines;
   removing the solvent and ammonia;
   dissolving the residue in anhydrous methanol;
   adding hydrogen chloride and reacting to remove the 3'-N-Boc group;
   concentrating the solution;
   isolating the product with preparative HPLC;
   converting the product to the hydrochloride of the 5-imino-13-deoxy anthracycline product.

4. The process according to claim 3, wherein said reduction solution has a pH of about 7.0 or less.

5. The process according to claim 4, wherein said refluxing is carried out at a temperature of from about 68° C. to about 72° C.

6. The process according to claim 4, wherein said refluxing is carried out at a temperature of from about 65° C. to about 75° C.

7. The process according to claim 3, wherein said refluxing is carried out at a temperature of up to about 75° C.

8. The process according to claim 3, wherein said refluxing is carried out in an absence of oxygen.

9. The process according to claim 3, wherein said refluxing is carried out in an absence of water.

10. The process according to claim 3, wherein said refluxing is carried out in an atmosphere of nitrogen.

11. The process according to claim 3, wherein said refluxing is carried out in an atmosphere of an inert gas.

12. The process according to claim 3, wherein the amination is carried out at about 0–4° C.

13. The process according to claim 3, wherein the amination is carried out in the absence of water.

14. The process according to claim 3, wherein said processes result in a yield of the 5-imino-13-deoxy anthracycline derivative of from about 40% to about 50%.

15. The compounds according to claim 1, wherein $R_1$ is OMe, $R_2$ is OH, and $R_3$ is OH, and $R_4$ is

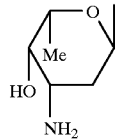

16. The compounds according to claim 1, wherein $R_1$ is OMe, $R_2$ is OH, and $R_3$ is H, and $R_4$ is

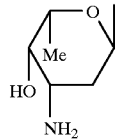

17. The compounds according to claim 1, wherein $R_1$ is OH, $R_2$ is OH, and $R_3$ is H, and $R_4$ is

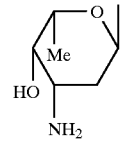

18. The compounds according to claim 1, wherein $R_1$ is OMe, $R_2$ is OH, and $R_3$ is OH, and $R_4$ is

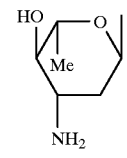

19. The compounds according to claim 1, wherein $R_1$ is H, $R_2$ is OH, and $R_3$ is H, and $R_4$ is

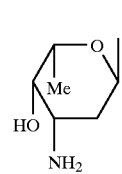

20. The compounds according to claim 1, wherein $R_1$ is H, $R_2$ is OH, and $R_3$ is OH, and $R_4$ is

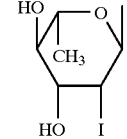

* * * * *